(12) United States Patent
Creighton, IV et al.

(10) Patent No.: US 6,537,196 B1
(45) Date of Patent: Mar. 25, 2003

(54) MAGNET ASSEMBLY WITH VARIABLE FIELD DIRECTIONS AND METHODS OF MAGNETICALLY NAVIGATING MEDICAL OBJECTS

(75) Inventors: Francis M. Creighton, IV, St. Louis, MO (US); Roger N. Hastings, Maple Grove, MO (US); Andrew F. Hall, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/695,119

(22) Filed: Oct. 24, 2000

(51) Int. Cl.[7] .............. A61N 2/00; A61B 5/05; A61B 19/00; H01F 7/00
(52) U.S. Cl. .......... 600/12; 600/424; 128/897; 335/209
(58) Field of Search .............. 600/9, 12, 14, 600/15, 407, 424, 415, 410, 425, 476; 661/15; 310/181, 1; 128/897; 335/209–220, 222, 223, 306, 298, 302; 210/220

(56) References Cited

U.S. PATENT DOCUMENTS

| | | | | |
|---|---|---|---|---|
| 3,358,676 A | * | 12/1967 | Frei et al. ............... | 600/12 |
| 4,727,857 A | * | 3/1988 | Hörl ....................... | 600/15 |
| 4,862,128 A | * | 8/1989 | Leupold .................. | 335/306 |
| 5,387,176 A | * | 2/1995 | Markoll .................. | 600/14 |
| 5,437,600 A | * | 8/1995 | Liboff et al. ............. | 600/9 |
| 5,441,495 A | * | 8/1995 | Liboff et al. ............. | 600/9 |
| 5,463,263 A | * | 10/1995 | Flynn .................... | 310/181 |
| 5,589,065 A | * | 12/1996 | Bogatin et al. ......... | 210/222 |
| 5,632,720 A | * | 5/1997 | Kleitz ................... | 601/15 |
| 6,001,055 A | * | 12/1999 | Souder .................. | 600/9 |
| 6,137,194 A | * | 10/2000 | Haugseth ............... | 310/1 |
| 6,212,419 B1 | * | 4/2001 | Blume et al. .......... | 600/407 |
| 6,263,230 B1 | * | 7/2001 | Haynor et al. ......... | 600/424 |
| 6,320,488 B1 | * | 11/2001 | Leupold ................ | 335/306 |

\* cited by examiner

Primary Examiner—Eric F. Winakur
Assistant Examiner—Nikita R Veniaminov
(74) Attorney, Agent, or Firm—Harness, Dickey & Pierce, P.L.C.

(57) ABSTRACT

An adjustable field magnet assembly comprising at least two magnets rotatably mounted so that the rotation of at least one of the at least two rotatably mounted magnets changes the magnetic field projected by magnet assembly. The magnet is particularly useful in providing a magnet field of variable direction for use in magnetically navigating medical objects in the body by rotating the magnets comprising the assembly and/or rotating the entire assembly.

35 Claims, 7 Drawing Sheets

MAGNET ASSEMBLY WITH VARIABLE FIELD DIRECTIONS AND METHODS OF MAGNETICALLY NAVIGATING MEDICAL OBJECTS

BACKGROUND OF THE INVENTION

This invention relates to magnets, and in particular to a magnet assembly that provides a variable magnetic field, and to a method of navigating medical devices using such a magnet assembly.

Permanent magnets are capable of providing strong magnetic fields useful in many applications. In some applications, such as in magnetic surgery, it is desirable from time to time to change the direction of the magnetic field. In the past this could only be accomplished by some combination of translations and rotations of the magnets. In the case of magnetic surgery, this means that a relatively large exclusion zone must be maintained around a patient. This exclusion zone interferes with the placement of other medical equipment, including imaging equipment necessary to monitor the magnetic surgery, and with access to the patient.

SUMMARY OF THE INVENTION

The assembly of the present invention comprises at least two rotatably mounted magnets having magnetization directions such that rotation of at least one of the magnets changes the direction of the magnetic field at an application point in the patient. Thus by a simple rotation of the magnets within the assembly the direction of the applied magnetic field can be changed, and the combination of rotating the magnets and rotating the magnet assembly allows a magnet field in virtually any direction, eliminating the need for large exclusion zones around the patient to accommodate translation of the magnet needed with prior art magnets.

BRIEF DESCRIPTION OF THE DRAWINGS

FIG. 19b is a perspective view of the ninth embodiment, with the single rotatable magnet in a different orientation than in FIG. 19a.

Corresponding reference numerals indicate corresponding parts throughout the several views of the drawings.

DETAILED DESCRIPTION OF THE INVENTION

Figure 1:
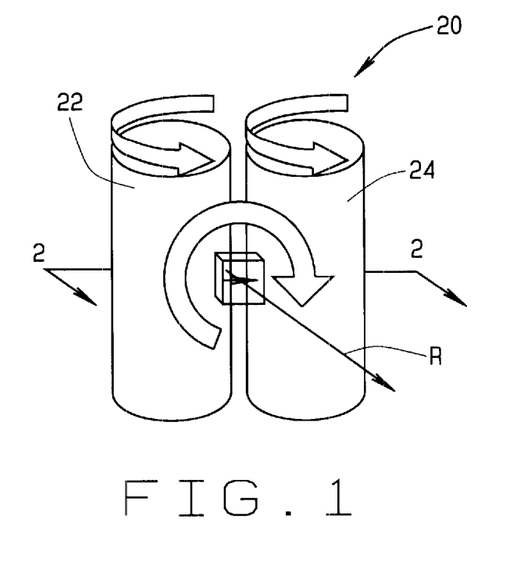
FIG. 1 is a schematic diagram of a first embodiment of a magnet assembly comprising two magnet cylinders constructed according to the principles of this invention.

A first embodiment of a magnet assembly, indicated generally as 20, is shown schematically in FIG. 1. The assembly 20 comprises two rotatably mounted, generally parallel magnet cylinders 22 and 24. Each of the cylinders 22 and 24 is made from a permanent magnetic material, such as NdBFe, or other magnetic material, preferably a high energy producing material with high coercivity. As described below is preferably jacketed in nonmagnetic stainless steel or wrapped in high strength carbon fiber or other strong nonmagnetic material. Each of the magnet cylinders 22 and 24 is rotatable about its longitudinal axis. As shown and described herein the magnet cylinders 22 and 24 have a generally circular cross-section which is preferred because of ease of construction and because the magnets can be closely spaced and rotated without mutual interference. However, the cylinders could have some other cross-sectional profile. Further, each of the magnet cylinders 22 and 24 is preferably uniformly magnetized in one direction, perpendicular to its longitudinal axis. For particularly applications, however, it may be desirable to have regions with differing magnetization directions, for example varying across the cross-section of the magnet cylinder, or varying along the length of the cylinder to increase the focused field effect of the assembly. While the magnet assemblies shown and described herein are particularly useful for magnetic medical procedures, such as navigation and aneurysm filling, the invention is not so limited, and the magnetic assemblies can be used in any application where a variable focused field is needed.

Together the magnet cylinders 22 and 24 create a magnetic field in the operating region O sufficient to magnetically navigate a medical device inside the body. The operating region O is preferably a generally cubic region at least about 3 inches by about 3 inches by about 3 inches, and more preferably at least about 6 inches by about 6 inches by about 6 inches. The operating region O is preferably at least about 7 inches from the magnet cylinders 22 and 24, and more preferably at least about 10 inches from the magnet cylinders so that the operating region can be used to magnetically navigate magnetic materials anywhere in the body.

Figure 2A:
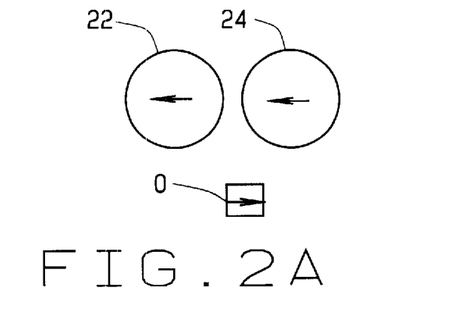
FIG. 2a is a horizontal cross-sectional view of the magnet assembly, taken along the plane of line 2—2 in FIG. 1, illustrating the field direction created in an operating region by the magnet cylinders in a first configuration.
Figure 2B:
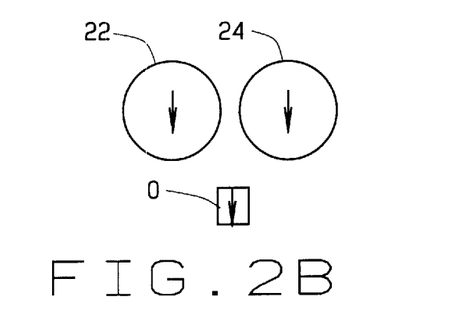
FIG. 2b is a horizontal cross-sectional view of the magnet assembly, taken along the plane of line 2—2 in FIG. 1, illustrating the field direction created in an operating region by the magnet cylinders in a second configuration.
Figure 2C:
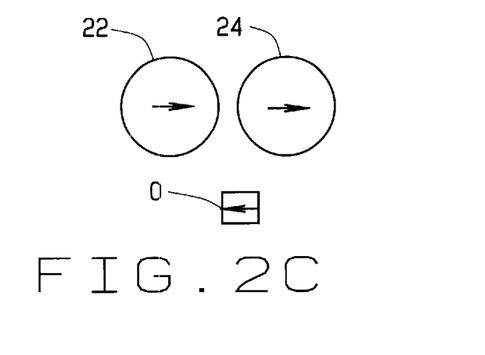
FIG. 2c is a horizontal cross-sectional view of the magnet assembly, taken along the plane of line 2—2 in FIG. 1, illustrating the field direction created in an operating region by the magnet cylinders in a third configuration.
Figure 2D:
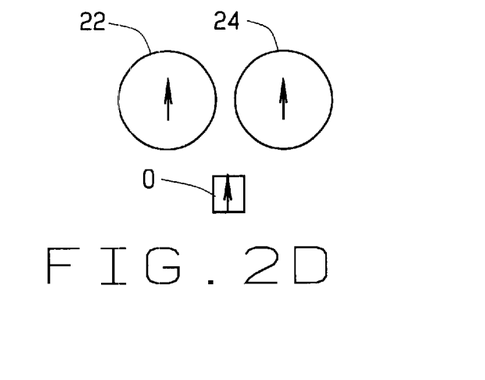
FIG. 2d is a horizontal cross-sectional view of the magnet assembly, taken along the plane of line 2—2 in FIG. 1, illustrating the field direction created in an operating region by the magnet cylinders in a fourth configuration.

The magnetic field created by the magnet cylinders 22 and 24 is preferably at least 0.1 T. in any direction in the plane of the magnetization directions of the cylinders, by rotating the cylinders. This is illustrated in FIGS. 2a, 2b, 2c, and 2d, wherein the magnet cylinders 22 and 24 are shown in FIG. 2a in a configuration that creates a magnetic field generally toward the magnet assembly, in FIG. 2b in a configuration that creates a magnet field parallel to the plane of the cylinders, in FIG. 2c in a configuration that creates a magnet field away from the magnet assembly, and in FIG. 2d in a configuration that creates a magnet field in a direction parallel to the plane of the magnets, but opposite from the direction shown in FIG. 2b. The magnetization direction of the magnet cylinders is represented by the arrow superimposed over the cylinder, and the magnetic field direction is represented by the arrow superimposed over the box representing the operating region. Is to be understood that arrangements of the magnetization of individual magnets beyond those of FIGS. 2a, 2b, 2c, 2d and are possible and necessary in order to provide all directions of magnetic field in a plane parallel to the magnets but within the operating region O. In other words, the two magnets in ordinary use will not have their magnetizations parallel as shown in these figures.

By rotating the assembly 20 about an axis R that is perpendicular to the plane of the cylinders 22 and 24, a magnetic field direction can be created in the operating region in any direction. This is illustrated by comparing FIG. 1 and FIG. 3, where rotation of the magnet assembly 20 rotates the magnetic field direction in a plane parallel to the plane of the magnet cylinders.

Figure 3:
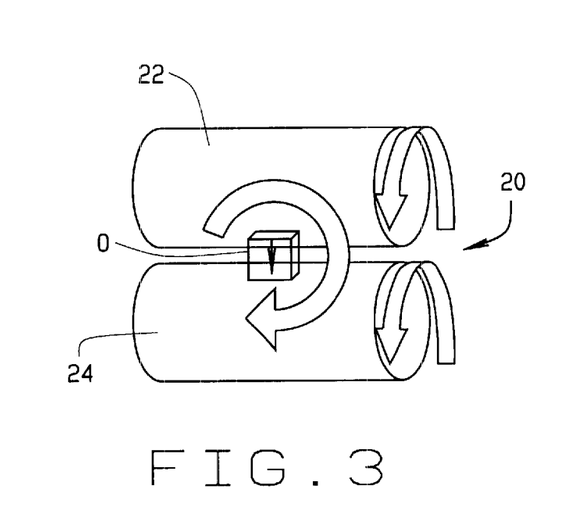
FIG. 3 is a schematic diagram of the magnet assembly of FIG. 1, rotated about an axis perpendicular to the plane of the magnet cylinders.

Thus, through a combination of rotations of the magnet cylinders 22 and 24 about their respective axes, and the rotation of the assembly 20 about axis R, a magnetic field can be created in the portion of the body containing the operating region O in any direction, without the need to translate the assembly 20. This means that exclusion zone around the magnet assembly 20 is much smaller than with other types of magnets which must accommodate translations in all directions in the plane of the magnet in order to provide all directions of field lines. Thus, the assembly 20 allows for better access to the patient, and better accommodates other equipment in the operating room, including imaging equipment such as bi-plane fluoroscopic imaging equipment.

Figure 4:
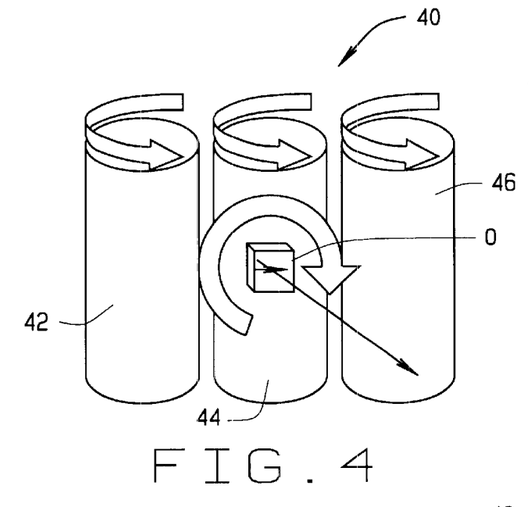
FIG. 4 is a schematic diagram of a second embodiment of a magnet assembly comprising three magnet cylinders constructed according to the principles of this invention.

A second embodiment of a magnet assembly, indicated generally as 40, is shown schematically in FIG. 4. The assembly 40 comprises three rotatably mounted, parallel magnet cylinders 42, 44, and 46. The cylinders 42, 44, and 46 are preferably arranged in a plane. Each of the cylinders 42, 44 and 46 is made from a permanent magnetic material, such as NdBFe, which as described below is preferably jacketed in stainless steel, carbon fibers or other strong, nonmagnetic material. As described above with respect to assembly 20, the cylinders 42, 44 and 46 may have a circular cross-section, or a cross-section of some other shape. Each of the magnet cylinders 42, 44, and 46 is rotatable about its longitudinal axis. Further, each of the magnet cylinders 42, 44, and 46 is preferably uniformly magnetized in one direction, perpendicular to its longitudinal axis. As described above with respect to assembly 20, the magnetization may vary through the cylinders.

Together the magnet cylinders 42, 44, and 46 create a magnetic field in the operating region O sufficient to magnetically navigate a magnetic object, such as a medical device inside the body. The operating region O is preferably a generally cubic region at least about 3 inches by about 3 inches by about 3 inches, and more preferably at least about 6 inches by about 6 inches by about 6 inches. The operating region O is preferably at least about 7 inches from the magnetic cylinders, and more preferably at least about 10 inches from the magnet cylinders 42, 44 and 46 so that it can be used to magnetically navigate magnetic materials anywhere in the body.

Figure 5A:
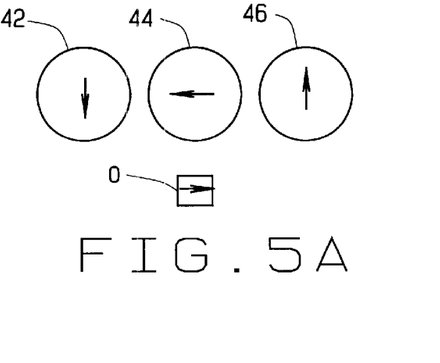
FIG. 5a is a horizontal cross-sectional view of the magnet assembly, taken along the plane of line 5—5 in FIG. 4, illustrating the field direction created in an operating region by the magnet cylinders in a first configuration.
Figure 5B:
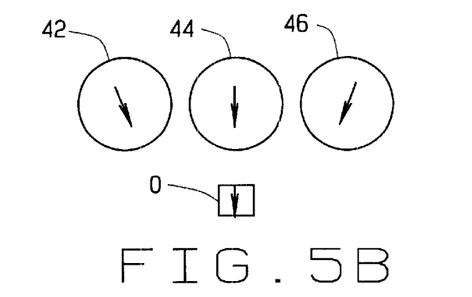
FIG. 5b is a horizontal cross-sectional view of the magnet assembly, taken along the plane of line 5—5 in FIG. 4, illustrating the field direction created in an operating region by the magnet cylinders in a second configuration.
Figure 5C:
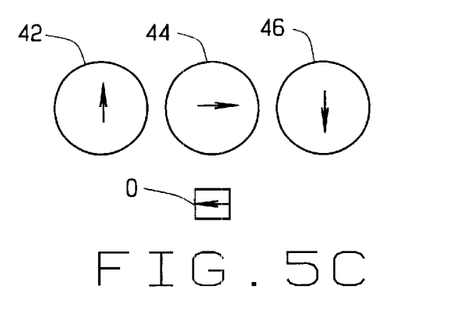
FIG. 5c is a horizontal cross-sectional view of the magnet assembly, taken along the plane of line 5—5 in FIG. 4, illustrating the field direction created in an operating region by the magnet cylinders in a third configuration.
Figure 5D:
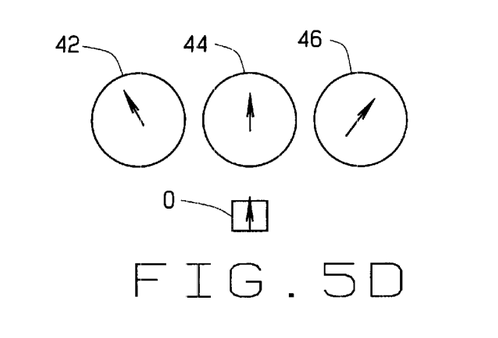
FIG. 5d is a horizontal cross-sectional view of the magnet assembly, taken along the plane of line 5—5 in FIG. 4, illustrating the field direction created in an operating region by the magnet cylinders in a fourth configuration.

The magnetic field created by the magnet cylinders 42, 44, and 46 is preferably at least 0.1 T. in any direction in the plane of the magnetization directions of the cylinders, by rotating the cylinders. This is illustrated in FIGS. 5a, 5b, 5c, and 5d, wherein the magnet cylinders 42, 44 and 46 are shown in FIG. 5a in a configuration that creates a magnetic field generally toward the magnet assembly, in FIG. 5b in a configuration that creates a magnet field parallel to the plane of the cylinders, in FIG. 5c in a configuration that creates a magnet field away from the magnet assembly, and in FIG. 5d in a configuration that creates a magnet field in a direction parallel to the plane of the magnets, but opposite from the direction shown in FIG. 5b. Is to be understood that arrangements of the magnetization of individual magnets beyond those of FIGS. 5a, 5b, 5c, 5d and are possible and necessary in order to provide all directions of magnetic field in a plane parallel to the magnets but within the operating region O. In other words, the three magnets in ordinary use will not have their magnetizations parallel as shown in these figures.

By rotating the assembly about an axis R that is perpendicular to the plane of the cylinders 42, 44, and 46, a magnetic field direction can be created in the operating region in any direction. This is illustrated by comparing FIG. 4 and FIG. 6, where rotation of the magnet assembly 40 rotates the magnetic field direction in a plane parallel to the plane of the magnet cylinders 42, 44 and 46.

Figure 6:
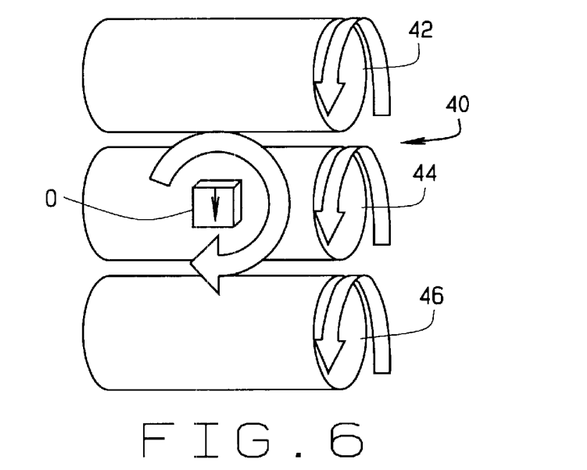
FIG. 6 is a schematic diagram of the magnet assembly of FIG. 4, rotated about an axis perpendicular to the plane of the magnet cylinders.

Thus, through a combination of rotations of the magnet cylinders 42, 44 and 46 about their respective axes, and the rotation of the assembly about axis R, a magnetic field can be created in the portion of the body containing the operating region O in any direction, without the need to translate the assembly 40. This means that exclusion zone around the magnet assembly 40 is much smaller than with other types of magnets which must accommodate some translation of the magnet. Thus, the assembly 40 allows for better access to the patient, and better accommodates other equipment in the operating room, including imaging equipment such as bi-plane fluoroscopic equipment.

Figure 7:
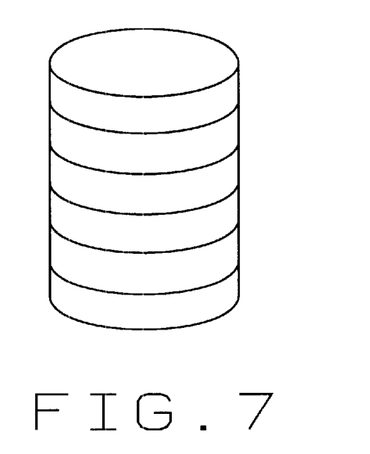
FIG. 7 is a perspective view of a stack of disk-shaped segments forming a magnet cylinder used in the magnet assemblies of the present invention.
Figure 8:
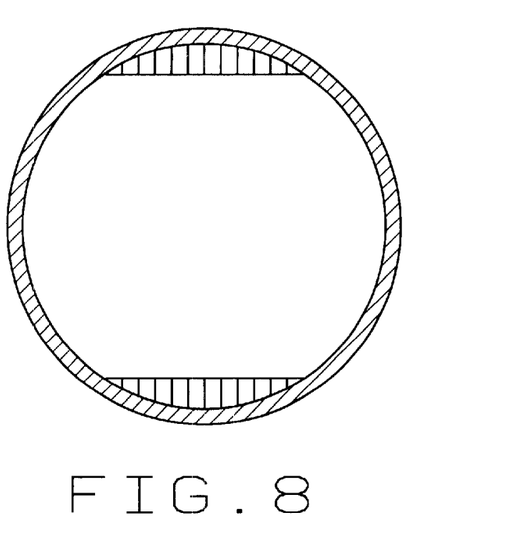
FIG. 8 is horizontal cross-sectional view through one of the rotatable cylinders.

The details of the preferred construction of the cylinders of the assemblies 20 and 40 are illustrated in FIGS. 7 and 8. Each of the cylinders is preferably made from a stack of generally disk shaped permanent magnets 60. Each of the disks 60 has a diameter of between about 4 inches and about 6 inches, and is between about ½ and about 2 inches thick. As best shown in FIG. 8, the disks 60 are stacked one upon the other, inside a cylindrical jacket 62, made of stainless steel or carbon fibers. The jacket 62 protects the disks 60, and helps to maintain their integrity despite the large forces to which they are exposed as cylinders rotate relative to one another. To maintain the proper configuration of the disks and prevent relative movement, the disks preferably have a flat 64 one the exterior that engages an insert 66 inside the jacket 62, to "key" the disks to facilitate rotation.

The cylinders comprising the assemblies of this invention are preferably rotatable about their longitudinal axis. The magnetization direction of the cylinders is preferably, but not necessarily uniform, and preferably, but not necessarily, perpendicular to the longitudinal axis.

The rotation of the cylinders in the assemblies, allows the magnet cylinders to create a magnetic field in the operating region in any direction from 0° to 360° in the plane of the magnetization directions of the cylinders. Furthermore, particularly with respect to magnet assembly 40, the magnet cylinders 42, 44, and 46 can be arranged so that they create a strong magnetic field in front of the assembly, and in particular in the operating region O. In this configuration, there is very weak magnetic field behind the assembly. However, through rotation of the cylinders 42, 44, and 46, this can be reversed, so that the strong field is behind the cylinders, and the weak field in front of the assembly, in effect "turning off" the magnet assembly from the perspective of the patient in front of the assembly.

In the preferred embodiment, the magnet assembly would be contained within a relatively compact enclosure. The rotation of the cylinders comprising the assembly, and the rotation of the assembly allow the assembly to create a magnetic field in the operating region in the patient in any direction. The enclosure hides the movement of the magnet, and protects the patient, and other people and equipment in the operating room, from the magnet.

Because a change of direction of the magnetic field can be quickly and easily effected by rotating the magnet cylinders and the assembly itself, the assembly is particularly amenable to automatic controls. Servo controls can be provided to rotate the individual cylinders about their respective axes and to rotate the assembly about axis R. A direction can be input into a control system by the physician, for example using a mouse on the two images of a bi-planar fluoroscopic imaging system, or using a joystick or keyboard. A computer can then calculate the best combination of rotational directions of the cylinder magnetizations and rotation of the assembly to achieve the desired direction. The computer can even account for a desired lead angle to ensure the proper navigation of a magnetic object in the body. An automatic advancer can also be provided and coordinated by the computer control, so that once the proper magnetic field is applied, the object is advanced in the desired direction. Thus the magnet assembly of the present invention facilitates automating surgical procedures, and even facilitates telemedical procedures, where a procedure is performed by a physician remotely from the patient.

Figure 9A:
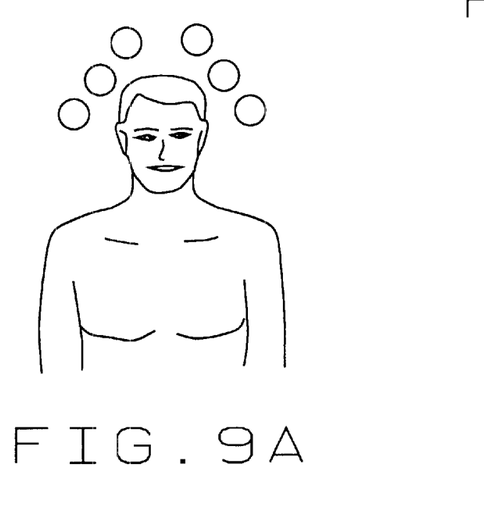
FIG. 9a is a front elevation schematic diagram showing two assemblies configured to surround a patient's head.
Figure 9B:
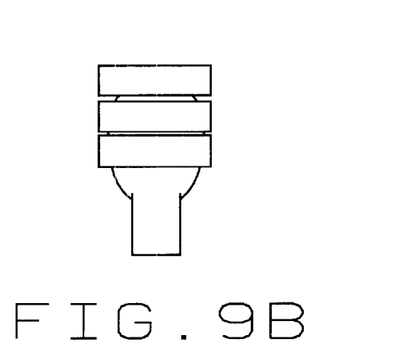
FIG. 9b is a side elevation schematic diagram of the two assemblies shown in FIG. 9, after rotation of the two assemblies relative to the patient.
Figure 9C:
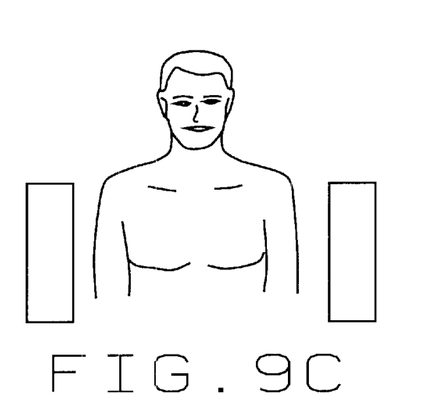
FIG. 9c is a top plan schematic diagram showing two assemblies configured to surround a patient's chest.
Figure 9D:
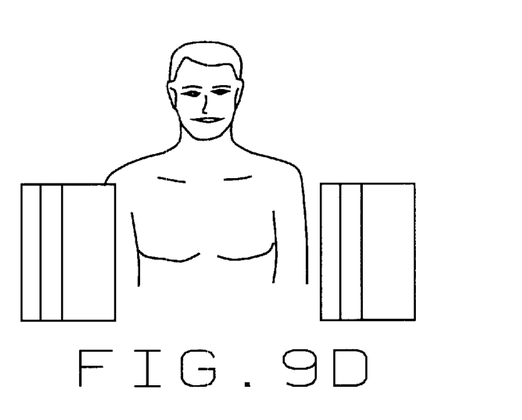
FIG. 9d is a top plan schematic diagram showing two assemblies tilted to accommodate movement of an imaging C-arm.

As shown in FIGS. 9a through 9d, a compound system with two planar magnetic assemblies and can be provided. As shown in FIGS. 9a and 9b, a compound system 100 has two planar magnetic assemblies 102 and 104 arranged at an angle with respect to each other. Thus the magnetic assemblies 102 and 104 form a concavity for receiving a portion of the body, such as the head. The combination of the two planes of magnet cylinders allows a stronger magnetic field to be applied further from the magnet assemblies. As shown in FIGS. 9c and 9d, a compound system 150 has two planar magnetic assemblies 152 and 154 arranged in generally parallel orientation on opposite sides of a patient's body, for example on opposite sides of a patient's chest for conducting a cardiac procedure. Because each magnet assembly 152 and 154 only has to project a magnetic field halfway through the patient, and because each magnet assembly only has to contribute half of the desired magnetic field, the combined weight of the two magnet assemblies on opposite sides of the patient can be less than the weight of a single magnet assembly on one side of the patient projecting the same magnetic field strength.

Figure 10:
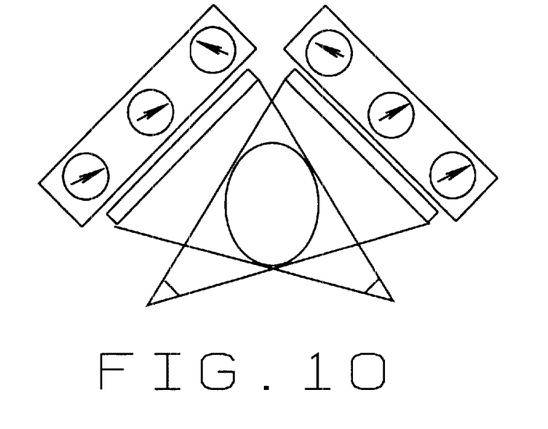
FIG. 10 is a schematic diagram of showing the arrangement of bi-planar imaging with two magnetic assemblies.

FIG. 10 shows a compound assembly 200, comprising two planar magnetic assemblies 202 and 204, arranged for bi-planar fluoroscopic imaging of the procedure site. Imaging plates 206 and 208, such as an amorphous silicon imaging plates (which are substantially unaffected by magnetic fields), are disposed in front of each of the magnetic assemblies 203 and 204, respectively. Imaging beam sources, such as x-ray sources 210 and 212 are disposed to project an imaging beam through the patient and onto the imaging plates 206 and 208. Thus magnetic navigation can be provided while allowing access for fluoroscopic imaging.

Figure 11A:
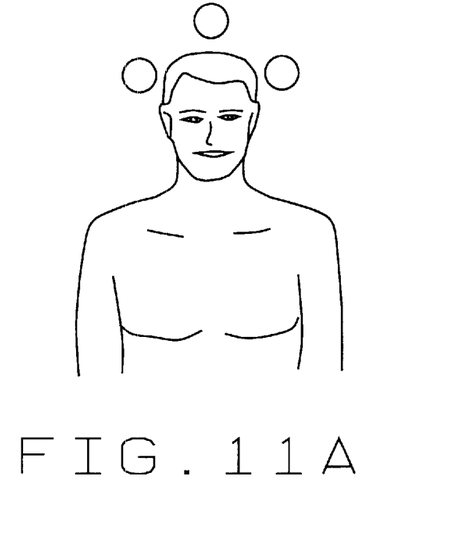
FIG. 11a is a front elevation schematic diagram of a third embodiment of a magnet assembly constructed according to the principles of this invention, comprising at least three non-coplanar magnet cylinders.
Figure 11B:
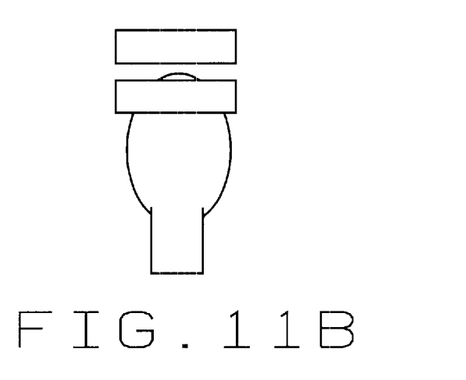
FIG. 11b is a side elevation view of the magnet assembly of the third embodiment.

A third embodiment of a magnet assembly constructed according to the principles of this invention as indicated generally is 220 in FIGS. 11a and 11b. The assembly 220 comprises at least three parallel, rotatably mounted magnet cylinders 222, 224 and 226. Each of the magnet cylinders 222, 224 and 226 is preferably constructed as described above, with a magnetization direction generally perpendicular to the longitudinal axis of the cylinder. The cylinders are arranged so they are not coplanar but instead form a concave portion for receiving a portion of the patient's body. As shown in FIGS. 11a and 11b, the cylinders 222, 224 and 226 form a concavity for receiving the patient's head. Rotation of the cylinders 222, 224, and 226 and rotation of the assembly (compare FIGS. 11a and 11b) allows the creation of a magnetic field in any selected direction in an operating region in the part of the patient in the space between the cylinders 222, 224 and 226.

Figure 12:
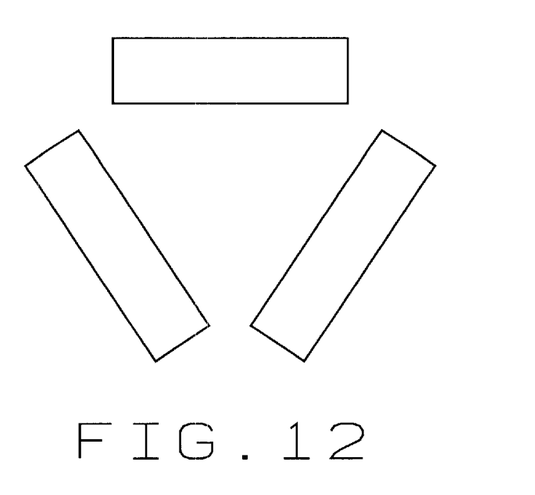
FIG. 12 is a top plan view of a fourth embodiment of a magnet assembly constructed according to the principles of this invention, in which the magnetic rollers are in a non-parallel, planar configuration.
Figure 13:
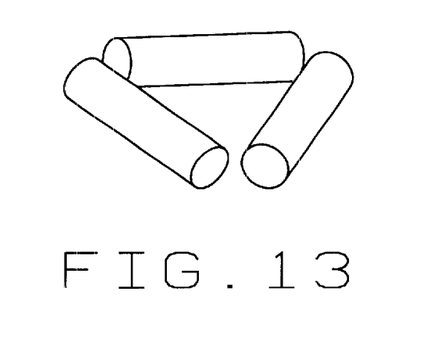
FIG. 13 is a perspective view of the magnet assembly of the fourth embodiment.

A fourth embodiment of a magnet assembly constructed according to the principles of this invention is indicated generally as 250 in FIGS. 12 and 13. The assembly 250 comprises three magnet cylinders 252, 254, and 256, whose longitudinal axes are coplanar. Each of the magnet cylinders is preferably constructed as described above, with a magnetization direction generally perpendicular to the longitudinal axis. In this arrangement, rotation of the cylinders 252, 254, and 256 can project a magnetic field in an operating region spaced from the plane of the cylinders in any direction. Thus the magnet assembly 250 can provide a navigating magnetic field in any direction without any translation or rotation of the assembly, but simply a rotation of the cylinders 252, 254, and 256 comprising the assembly.

Figure 14:
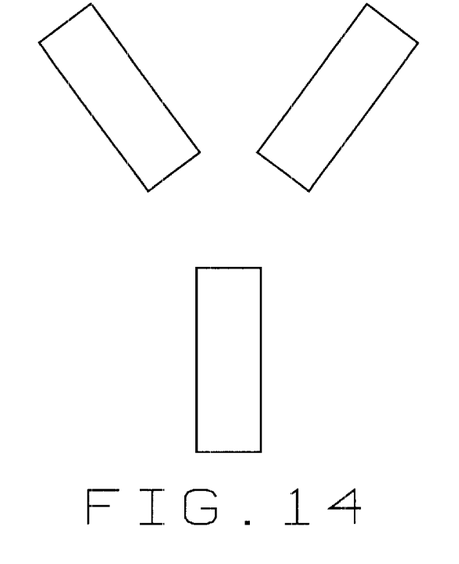
FIG. 14 is a top plan view of a fifth embodiment of a magnet assembly constructed according to the principles of this invention, in which the magnet rollers are in a non-parallel, planar configuration.
Figure 15:
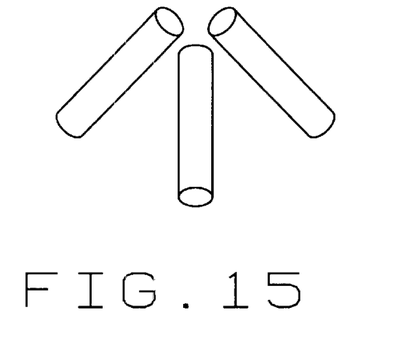
FIG. 15 is a perspective view of the magnet assembly of the fifth embodiment.
Figure 16A:
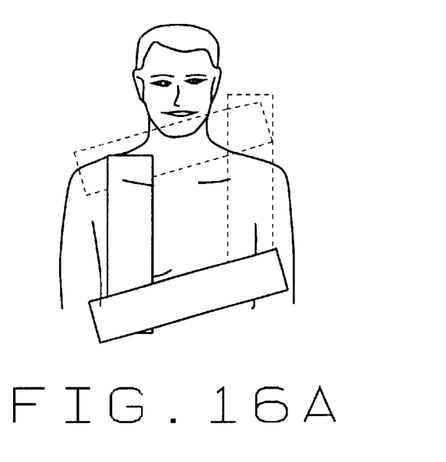
FIG. 16a is top plan view of a six embodiment of a magnet assembly constructed according to the principles of this invention, with a patient disposed within the magnet assembly.
Figure 16B:
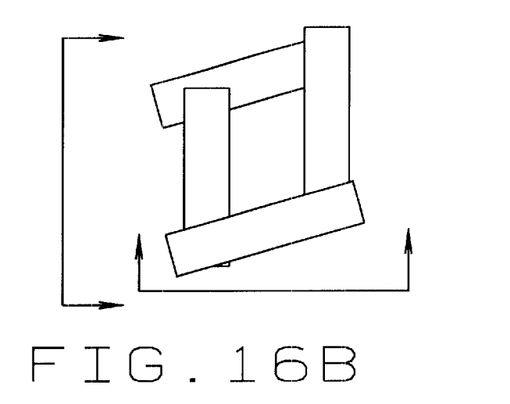
FIG. 16b is a top plan view of the magnet assembly of the sixth embodiment, without the patient.
Figure 16C:
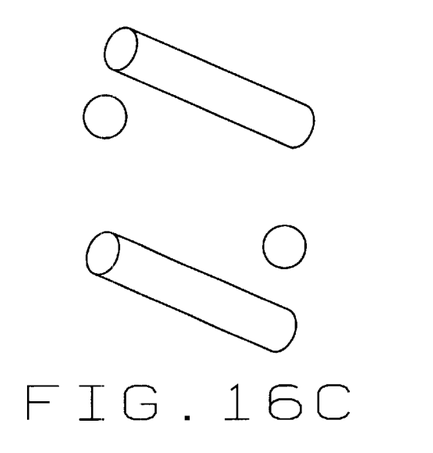
FIG. 16c is an end elevation of the magnet assembly of the sixth embodiment, taken along the plane of line 16c—16c in FIG. 16b.
Figure 16D:
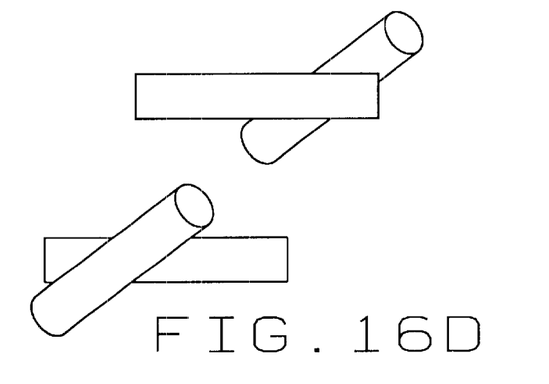
FIG. 16d is a side elevation view of the magnet assembly of the sixth embodiment, taken along the plane of line 16d—16d in FIG. 16c.

A fifth embodiment of a magnet assembly constructed according to the principles of this invention is indicated generally as 300 in FIGS. 14 and 15. The assembly 300 comprises three magnet cylinders 302, 304, and 306, arranged generally in a "Y" shaped configuration. Each of the magnet cylinders is preferably constructed as described above, with a magnetization direction generally perpendicular to the longitudinal axis. The magnet cylinders 302, 304, and 306 may be coplanar, or as shown in FIGS. 14 and 15, the magnet cylinders may be arranged in a pyramid, with one end of each of magnet cylinders at the apex of the pyramid. In this arrangement, the cylinders form a concave space for receiving a portion the patient's body. The magnet assembly 300 can provide a navigating magnetic field in any direction without any translation or rotation of the assembly, but simply a rotation of the cylinders 302, 304, and 306.

A sixth embodiment of a magnet assembly constructed according to the principles of this invention is indicated generally as 350 in FIGS. 16a through 16d. The magnet assembly comprises four magnet cylinders 352, 354, 356, and 358. The first magnet cylinder 352 extends generally transversely across the top of the user's body, below the chest. The second magnet cylinder 354 extends generally transversely below the patient's body, above the shoulders. The third magnet cylinder 356, extend generally parallel with the longitudinal of the patient, above the right side of the patient's chest. The fourth magnet cylinder 358 extends generally parallel with the longitudinal axis of the patient, below the right side of the patient's chest. The left end of the cylinder 352 extends over the bottom end of the cylinder 356, and the cylinder slopes downwardly toward the right side. The right end of the second magnet cylinder 354 is above the upper end cylinder 358, and the cylinder slopes downwardly toward the left side. Each of the cylinders is preferably constructed as described above, with the magnetization direction generally perpendicular to the longitudinal axis of the cylinder. The first and second cylinders 352 and 354, and the third and fourth cylinders 356 and 358, are arranged on opposite sides of the heart while leaving the heart uncovered so that the heart can be imaged during the procedure. Rotation of the cylinders 352, 354, 336 and 358 allows the creation of a magnetic field in any selected direction in the operating region (the heart in FIGS. 16a–16d).

Figure 17A:
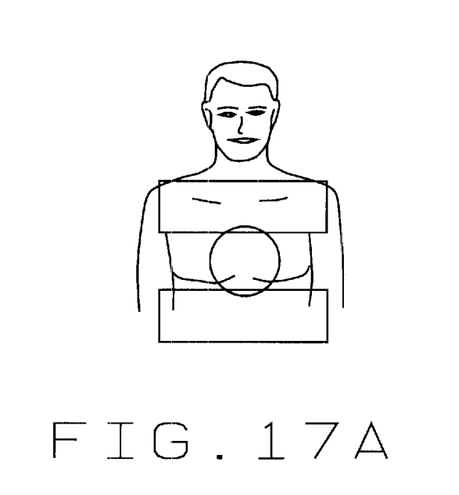
FIG. 17a is a top plan view of a seventh embodiment of a magnet assembly, comprising four magnets, but with only the two magnets disposed below the patient shown for clarity.
Figure 17B:
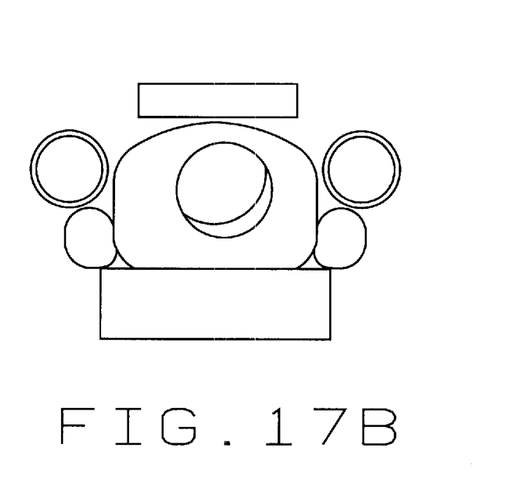
FIG. 17b is a transverse cross-sectional view of the magnetic assembly of the seventh embodiment.

An eighth embodiment of a magnet assembly constructed according to the principles of this invention is indicated generally as 400 in FIGS. 17a and 17b. The magnet assembly 400 comprises first and second cylinders 402 and 404 beneath the patient, the first roller extending generally below the shoulders at the top of the chest, and the second cylinder extending generally below the rib cage at the bottom of the chest. The cylinders are constructed as described above, with the magnetization direction generally perpendicular to the longitudinal axis of the cylinder. The magnet assembly 400 further comprises third and fourth rollers 406 and 408 (shown only in FIG. 17b), extending parallel to the longitudinal axis of the patient, on either side of the patient, above the patient's arms. The cylinders 402 and 404 are spaced such that an imaging beam source below the patient, and an imaging plate, such as an amorphous silicon imaging plate 410 above the patient, can image the heart H without interference from the cylinders. Rotation of the cylinders 402, 404, 406, 408 allows the creation of a magnetic field, in any selected direction in the operating region (the heart in FIGS. 17a and 17b).

Figure 18A:
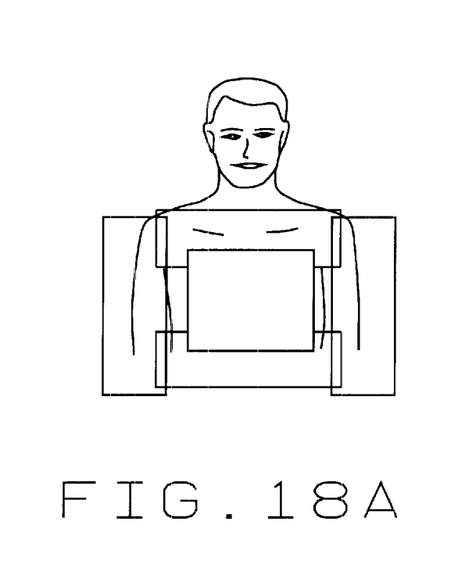
FIG. 18a is a top plan view of an eighth embodiment of a magnet assembly.
Figure 18B:
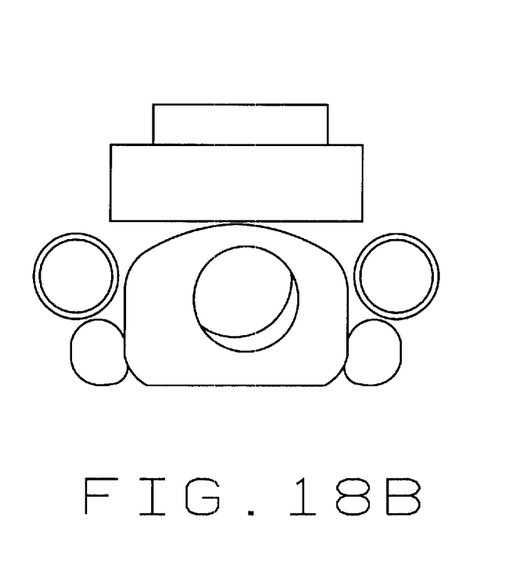
FIG. 18b is a transverse cross-sectional view of the magnet assembly of the eighth embodiment.

An eight embodiment of a magnet assembly constructed according to the principles of this invention is indicated generally as 450 in FIGS. 18a and 18b. The assembly 450 is similar in construction to assembly 400, comprising first and second cylinders 452 and 454, extending generally transversely across the patient's body. However, unlike assembly 400 wherein the first and second cylinders 402 and 404 are below the patient, cylinders 452 and 454 are above the patient. The magnet assembly 450 also includes third and fourth magnet cylinders 456 and 458, which like cylinders 406 and 408 of assembly 400, extend parallel to the longitudinal axis of the patient, on either side of the patient above the patient's arms. The cylinders 452 and 454 are spaced such that an imaging beam source below the patient, and an imaging plate, such as an amorphous silicon imaging plate 460 above the patient, can image the heart without interference from the cylinders. The assembly 450 is particularly adapted to be mounted on a ceiling support, and lowered into position over the patient, and raised away from the patient after completion of the procedure. Rotation of the cylinders 452, 454, 456 and 458 allow the creation of a magnetic field in any selected direction of the operating region (the heart in FIGS. 18a and 18b).

Figure 19A:
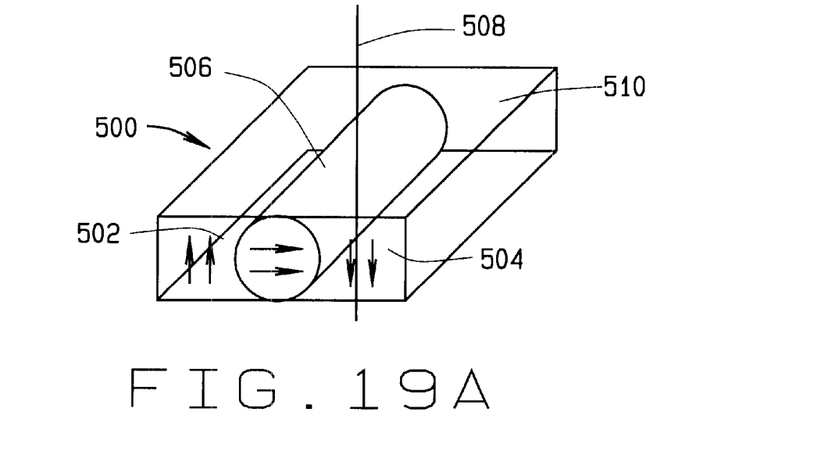
FIG. 19a is a perspective view of a ninth embodiment of a magnet assembly constructed according to the principles of this invention, having a single rotatable magnet.
Figure 19B:
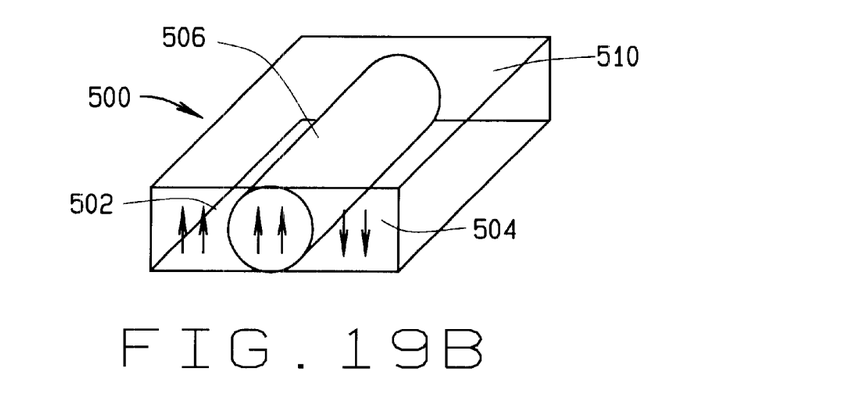
Figure 19C:
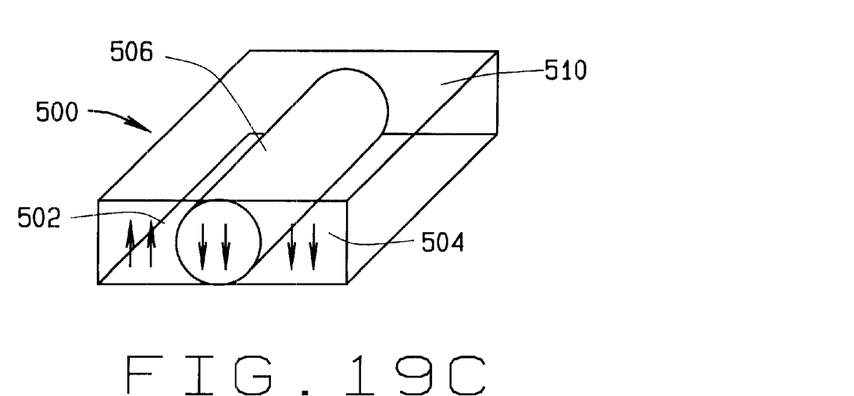
FIG. 19c is a perspective view of the ninth embodiment, with the single rotatable magnet in a different orientation than in FIGS. 19a and 19b.

A ninth embodiment of a magnet assembly constructed according to the principles of this invention is indicated generally as 500 in FIGS. 19a, 19b, and 19c. As shown in FIGS. 19a through 19c, the magnet assembly comprises at least two magnets, at least one of which is rotatable with respect to the other to change the direction and/or intensity of the magnetic field in an operating region spaced from the face 510 of the assembly, preferably along a central perpendicular axis 508. In the preferred embodiment there are three magnets 502, 504, and 506. As shown in FIGS. 19a through 19c, the magnets 502 and 504 are stationery, and magnet 506 is mounted for rotation relative to the magnets 502 and 504. As shown in the Figures, the magnets 502 and 504 are formed in one piece, with an opening for receiving the magnet 506, but the invention is not so limited, and magnets 502 and 504 can be made in separate pieces. The magnet 502 is preferably magnetized parallel to the axis 508, and perpendicular to the face 510 of the assembly. The magnet 504 is likewise preferably magnetized parallel to the axis 508, and perpendicular to the face 510 of the assembly, but in a direction opposite to magnet 502. As shown in FIGS. 19a through 19c, the magnet 506 is preferably cylindrical (although it could be some other shape), and mounted for rotation about its longitudinal axis. The magnet 506 is preferably magnetized perpendicular to its axis of rotation.

As shown in FIGS. 19a through 19c, the rotation of the magnet 506 relative to the magnets 502 and 504 changes the magnetic field projected by the assembly. Thus by rotating the magnet 506, and by rotating the assembly 500 about axis 508, a magnetic field of sufficient strength for magnetic navigation of a magnet medical device can be projected in virtually any direction at an operating point space from the face 510 of the assembly. Operation In using the assemblies of this invention, a magnetically responsive medical device is introduced into the body. This device may be a cannula, catheter, endoscope, or other device that is magnetically responsive through the inclusion of an electromagnet, a permanent magnet, or a permeable magnetic material. The device is oriented in a desired direction by applying a magnetic field in the appropriate direction to cause the device to align in the desired direction. The applied field may be slightly different from the desired direction because of the properties of the device. Where the navigation is computer controlled, the computer can automatically take the properties of the device into account in determining the direction of the magnet field to apply. The magnet cylinders are turned and the magnet assembly is turned (where necessary) until the device is in the desired direction. The device can then be advanced, either manually or automatically, using an advancer. The device is advanced until a change of direction is desired. The assembly is used to apply a magnetic field to cause the device to orient in the new desired direction, and the device again advanced. This is repeated until the device is in the desired location.

We claim:

1. A magnet assembly that projects a magnetic field of variable direction, the assembly comprising at least two magnets arranged generally side by side, with, at least one of the at least two magnets being rotatably mounted for rotation on an axis that does not extend through the other of the magnets independent of another of the at least two magnets to change the direction of the magnetic field projected by the assembly.

2. The magnet assembly according to claim 1 wherein the magnet assembly projects a magnetic field of sufficient strength to orient a magnetic medical device.

3. The magnet assembly according to claim 1 wherein the magnet assembly projects a magnetic field of at least 0.1 Tesla at a sufficient distance from the assembly to orient a medical device in a body.

4. The magnet assembly according to claim 1 wherein there are two magnets, one of which is rotatably mounted.

5. The magnet assembly according to claim 1 wherein there are two magnets, each of which is independently rotatably mounted.

6. The magnet assembly according to claim 5 wherein the axes or rotation of the two magnets are parallel.

7. The magnet assembly according to claim 1 wherein there are three magnets, arranged generally in a plane, and wherein each of the three magnets is rotatably mounted on a different axis.

8. The magnet assembly according to claim 7 wherein the axes of rotation of the magnets are parallel.

9. A magnet assembly that projects a magnetic field of variable direction, the assembly comprising at least three magnets, arranged generally side by side, generally in a plane, and wherein at least one of the at least three magnets is rotatably mounted between two non-rotatably mounted magnets on an axis that does not extend through the other magnets.

10. A magnet assembly that projects a magnetic field of variable direction in an operating zone spaced from the assembly sufficiently so that the operating zone can be disposed inside a body for navigating a magnet medical device, the assembly comprising at least two magnets arranged generally side by side, at least one of which is rotatably mounted for rotation independent of at least one other magnet on an axis that does not extend through such other magnet to change the direction of the magnetic field projected by the assembly.

11. The magnet assembly according to claim 10 wherein the magnet assembly projects a magnetic field of sufficient strength to orient a magnetic medical device in the operating zone.

12. The magnet assembly according to claim 10 wherein the magnet assembly projects a magnetic field of at least 0.1 Tesla in the operating zone.

13. The magnet assembly according to claim 10 wherein there are two magnets, one of which is rotatably mounted.

14. The magnet assembly according to claim 10 wherein there are two magnets, both of which are rotatably mounted.

15. The magnet assembly according to claim 14 wherein the axes of rotation of the two magnets are parallel.

16. The magnet assembly according to claim 10 wherein there are at least three magnets, arranged generally in a plane, and wherein there is at least one rotatably mounted magnet, with a non-rotatably mounted magnet on either side of the at least one rotatably mounted magnet.

17. The magnet assembly according to claim 10 wherein there are three magnets, arranged generally in a plane, and wherein each of the magnets is rotatably mounted on a different axis.

18. The magnet assembly according to claim 17 wherein the axes of rotation of the magnets are parallel.

19. An adjustable field magnet assembly comprising at least two magnets independently rotatably mounted about different axes so that the rotation of at least one of the at least two rotatably mounted magnets changes the magnetic field projected by the magnet assembly in an operating region spaced from the assembly.

20. The adjustable field magnet assembly according to claim 19 wherein there are at least three rotatably mounted magnets.

21. The adjustable field magnet assembly according to claim 19 wherein the direction of magnetization of the magnets is generally perpendicular to the axis of rotation.

22. The adjustable field magnet assembly according to claim 19 wherein the direction of magnetization of each the magnets is uniform.

23. The adjustable field magnet assembly according to claim 19 wherein the direction of magnetization of each of the magnets is not uniform.

24. The adjustable field magnet assembly according to claim 19 wherein there are at least three rotatably mounted magnets, arranged in a plane.

25. The adjustable field magnet assembly according to claim 19 wherein the magnets are electromagnets.

26. An adjustable field magnet assembly comprising at least two magnets arranged side by side and independently rotatably mounted on different axes so that the rotation of at least one of the at least two rotatably mounted magnets changes the magnetic field projected by magnet assembly in an operating region spaced from the assembly the magnets being generally cylindrical permanent magnets fabricated from a primarily high-intrinsic coercive force material with a large residual induction field.

27. An adjustable field magnet assembly comprising at least two magnets arranged generally side by side and independently rotatably mounted on different axes so that the rotation of at least one of the at least two rotatably mounted magnets changes the magnetic field projected by magnet assembly in an operating region spaced from the assembly, the magnets being permanent magnets fabricated from a primarily high-intrinsic coercive force material with a large residual induction field.

28. An adjustable field magnet assembly comprising at least three magnets each independently rotatably mounted so that the rotation of at least one of the at least three rotatably mounted magnets changes the magnetic field projected by magnet assembly in an operating region spaced from the assembly the at least three magnets being arranged in a first plane, and at least three magnets arranged in a second plane, the first plane being adjacent to, and at angle with respect to the second plane, to define a treatment space therebetween.

29. An adjustable field magnet assembly comprising at least first and second magnet bodies, arranged generally side by side, at least one of which is rotatable independent of at least one other magnet body to change the magnetic field applied at an operating point spaced from the assembly.

30. A method of controlling a magnetically responsive element in the body, the method comprising applying a magnetic field to the object with a variable field magnet assembly having at least two independently rotatable magnetic elements, arranged side by side on different axes, and changing the direction of the magnetic field applied to the object by rotating at least one of the at least two independently rotatable magnetic elements.

31. The method of controlling a magnetically responsive element in the body according to claim 30, further comprising rotating the entire magnetic assembly.

32. The method according to claim 30 wherein the magnet assembly comprises at least two magnet elements independently rotatably mounted on parallel axes.

33. The method according to claim 30 wherein the magnet assembly comprises at least three magnets, arranged generally in a plane, and each rotably mounted on parallel axes.

34. The method according to claim 30 wherein a processor calculates the optimal combination of directions of magnetization of the individual magnets comprising the assembly so as to maximize the field strength at a given location in a patient, and further comprising rotating the magnets to the calculated combination of directions of magnetization of the individual magnets to yield the maximum field strength.

35. The method of claim 30 wherein a processor calculates the optimal combination of directions so as to include at least two successive motions of a guided element.

* * * * *